United States Patent
Godfrey, Jr. et al.

[11] Patent Number: 6,166,227
[45] Date of Patent: Dec. 26, 2000

[54] PREPARATION OF (S)-2-AMINO-6, 6-DIMETHOXYHEXANOIC ACID METHYL ESTER VIA NOVEL DIOXOLANES

[75] Inventors: Jollie D. Godfrey, Jr., Trenton, N.J.; David R. Kronenthal, Yardley; Mark D. Schwinden, Holland, both of Pa.

[73] Assignee: Bristol-Myers Squibb Co., Princeton, N.J.

[21] Appl. No.: 09/349,867

[22] Filed: Jul. 8, 1999

Related U.S. Application Data

[60] Provisional application No. 60/092,944, Jul. 15, 1998.

[51] Int. Cl.⁷ .................................................. C07D 317/00
[52] U.S. Cl. .......................................... 549/452; 549/451
[58] Field of Search ...................... 549/451, 452

[56] References Cited

U.S. PATENT DOCUMENTS

| | | | |
|---|---|---|---|
| 4,152,336 | 5/1979 | Kuroki et al. | 549/451 |
| 4,376,864 | 3/1983 | Drauz et al. | 549/373 |
| 4,397,677 | 8/1983 | Stach | 549/451 |
| 4,424,370 | 1/1984 | Kleeman et al. | 549/373 |
| 4,591,601 | 5/1986 | Maryanoff et al. | 549/451 |
| 5,332,826 | 7/1994 | Buckland | 546/330 |
| 5,508,272 | 4/1996 | Robl | 514/80 |
| 5,670,666 | 9/1997 | Hou et al. | 549/451 |

FOREIGN PATENT DOCUMENTS

| | | |
|---|---|---|
| 181675B | 5/1986 | European Pat. Off. |
| 307023 | 3/1989 | European Pat. Off. |
| 383403 | 8/1990 | European Pat. Off. |
| 905257 | 3/1999 | European Pat. Off. |
| 919630 | 6/1999 | European Pat. Off. |
| 972845 | 1/2000 | European Pat. Off. |
| 11-140076A | 5/1999 | Japan . |
| 11-140077A | 5/1999 | Japan . |
| 11-206397A | 8/1999 | Japan . |
| WO98/48040 | 10/1998 | WIPO . |
| WO99/35145 | 7/1999 | WIPO . |
| WO00/04179 | 1/2000 | WIPO . |
| WO00/14265 | 3/2000 | WIPO . |

OTHER PUBLICATIONS

Frankel et al, "Poly–condensation of a α–Amino Acid Esters . . . " JACS, vol. 64, p. 2264–2268 (1942).

Almeida et al, "New Enantioselective Synthesis . . . " Tetrahedron Asymmetry, vol. 3, No. 11, p. 1431–1440 (1992).

Meyers et al, "A One Step Synthesis of Pseudoephedrine Glycinamide . . . ", Tetrahedron Letters, vol. 36, No. 26, p. 4555–4558 (1995).

Rumbero et al., Bioorganic & Medicinal Chem., vol. 3, p. 1237–1240 (1995).

Sham et al., J. Chem. Soc., Chem. Commun., p. 1792–1793 (1987).

Johnson et al., J. Org. Chem., vol. 27, p. 798–802 (1962).

*Primary Examiner*—Amelia Owens
*Attorney, Agent, or Firm*—Stephen B. Davis

[57] ABSTRACT

The glycinamide of the formula (I)

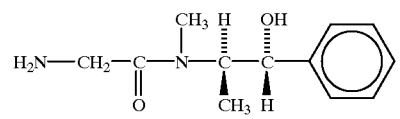

is reacted with the dioxolane of the formula (II)

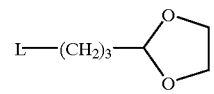

wherein L is a leaving group such as iodo, bromo, alkylsulfonyloxy, or arylsulfonyloxy to give the dioxolane of the formula (III)

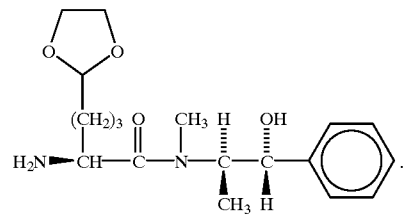

Treatment of (III) gives the dioxolane pentanoic acid IV

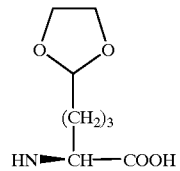

which can be converted to (S)-2-amino-6,6-dimethoxyhexanoic acid, methyl ester.

8 Claims, No Drawings

PREPARATION OF (S)-2-AMINO-6, 6-DIMETHOXYHEXANOIC ACID METHYL ESTER VIA NOVEL DIOXOLANES

This application claims priority from U.S. Provisional application Ser. No. 60/092,944 filed Jul. 15, 1998.

BACKGROUND OF THE INVENTION

Robl in U.S. Pat. No. 5,508,272 discloses compounds of the formula

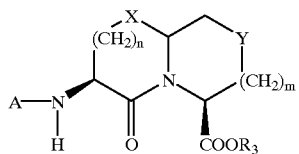

wherein A can be

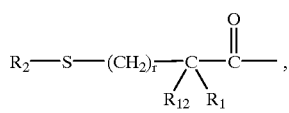

X can be S, Y can be $CH_2$, m can be one, and n can be two as possessing neutral endopeptidase and angiotensin converting enzyme inhibition activity. Among these compounds is [4S-[4α((R*),7α,10aβ]]-octahydro-4-[(2-mercapto-1-oxo-3-phenylpropyl-amino]-5-oxo-7H-pyrido[2,1-b][1,3] thiazepine-7-carboxylic acid which is currently undergoing clinical evaluation. This compound is reported in the literature as BMS 186,716 and as omapatrilat.

Robl discloses that the amino lactam portion of BMS 186,716, i.e. the intermediate

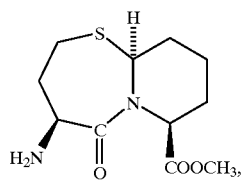

can be prepared by coupling (S)-2-amino-6,6-dimethoxyhexanoic acid, methyl ester with the N-protected amino acid

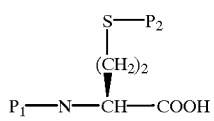

wherein $P_1$ is an amino protecting group and $P_2$ is a sulfur protecting group to give the dipeptide of the formula

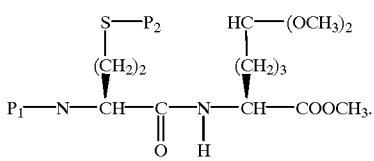

Removal of the $P_2$ protecting group, followed by acid catalyzed cyclization, and removal of the $P_1$ protecting group gives [4S-(4α, 7α, 10aβ)]-octahydro-4-amino-5-oxo-7H-pyrido[2,1-b][1,3]thiazepine-7-carboxylic acid, methyl ester.

Robl discloses preparing (S)-2-amino-6,6-dimethoxyhexanoic acid, methyl ester by converting N-protected L-ε-hydroxynorleucine to its methyl ester, oxidizing to the aldehyde of the formula

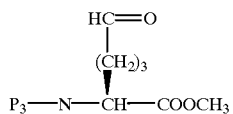

then reacting with trimethyl orthoformate in the presence of a strong acid catalyst, and removing the $P_3$ protecting group.

SUMMARY OF THE INVENTION

This invention is directed to an improved chemical synthesis of (S)-2-amino-6,6-dimethoxyhexanoic acid, methyl ester and novel dioxolane intermediates from this synthesis.

According to the process of this invention the glycinamide of the formula (I)

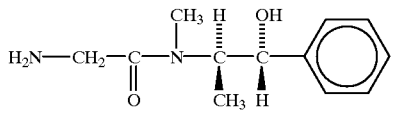

is reacted with the dioxolane of the formula (II)

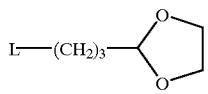

wherein L is a leaving group such as iodo, bromo, alkylsulfonyloxy, or arylsulfonyloxv to give the dioxolane of the formula (III)

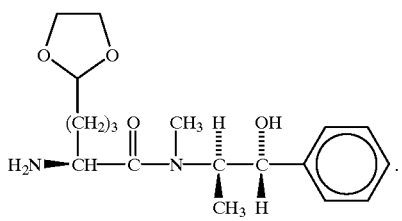

The dioxolane of formula III is treated under aqueous refluxing conditions to give the dioxolane pentanoic acid of the formula (IV)

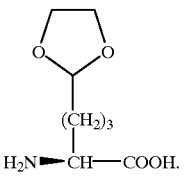

The dioxolane pentanoic acid of formula IV is then treated to exchange the dioxolane acetal with a dimethoxy acetal and convert the carboxylic acid to the methyl ester resulting in the desired compound (S)-2-amino-6,6- dimethoxyhexanoic acid, methyl ester. This can be achieved by reacting compound IV with thionyl chloride in methanol or by reacting compound IV with anhydrous HCl such as HCl gas and dimethyl sulfite in methanol or by the in situ generation of HCl such as by reacting compound IV with chlorotrimethylsilane or an acid chloride such as acetyl chloride and dimethyl sulfite in methanol.

Another aspect of this invention is the preparation of storage stable salts of (S)-2-amino-6,6-dimethoxyhexanoic acid, methyl ester of formula X. Such salts can be converted to the free amine for ultimate conversion to the desired product. This affords added flexibility in scheduling production runs and enables different stages of the reaction to be carried out at different manufacturing facilities.

DETAILED DESCRIPTION OF THE INVENTION (S)-2-Amino-6,6-dimethoxyhexanoic acid, methyl ester of the formula (X)

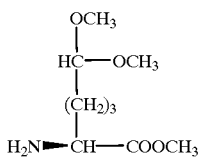

is useful as an intermediate in the preparation of [4S-[4α((R*),7α,10aβ]]-octahydro-4-[(2-mercapto-1-oxo-3-phenylpropyl)amino]-5-oxo-7H-pyrido[2,1-b]-[1,3]thiazepine-7-carboxylic acid of the formula (XI)

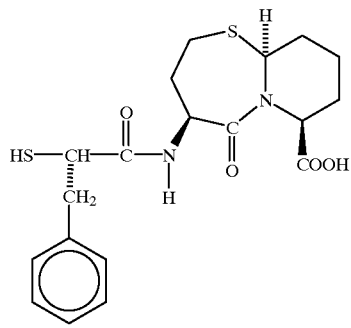

as described by Robl in U.S. Pat. No. 5,508,272.

According to the process of this invention (S)-2-amino-6,6-dimethoxyhexanoic acid, methyl ester of formula X is prepared by a chemical synthesis that avoids the need for an oxidation reaction and for an optical resolution. In this process, the glycinamide of formula I is reacted with the dioxolane of formula II to give the dioxolane of formula III. This reaction is performed in the presence of lithium diisopropylamide in an organic solvent such as tetrahydrofuran, which is preferred, diethoxymethane, tert-butyl methyl ether, 2-methyl tetrahydrofuran, or diethyl ether. The reaction is carried out at a temperature of from about −78° C. to about 0° C.

The glycinamide of formula I is prepared as described by Myers et al., *Tetrahedron Letters,* Vol. 36, p. 4555–4558 (1995).

The leaving group L in the dioxolane reagent of formula II can be an alkylsulfonyloxy such as methane sulfonyloxy, an arylsulfonyloxy such as p-toluenesulfonyloxy, bromo, or iodo with iodo being preferred. Such dioxolane reagents of formula II are known in the art or can be prepared from commercially available compounds. For example, the dioxolane of formula II wherein L is iodo can be prepared by reacting 2-(3-chloropropyl)-1,3-dioxolane with sodium iodide in the presence of sodium bicarbonate.

The dioxolane intermediate of formula III is then treated under aqueous refluxing conditions to give the dioxolane pentanoic acid of formula IV. The dioxolane pentanoic acid of formula IV is then reacted to give (S)-2-amino-6,6-dimethoxyhexanoic acid, methyl ester of formula X by exchanging the dioxolane acetal with a dimethoxy acetal and introducing the methyl ester group. For example, the dioxolane pentanoic acid of formula IV can be reacted with thionyl chloride in methanol or reacted with anhydrous HCl such as HCl gas and dimethyl sulfite in methanol or reacted with HCl generated in situ such as by reacting the compound of formula IV with chlorotrimethylsilane or an acid chloride such as acetyl chloride and dimethyl sulfite in methanol to give the desired compound of formula X. These reactions can be performed at a temperature of from about 40° C. to about 45° C.

(S)-2-Amino-6,6-dimethoxyhexanoic acid, methyl ester can be converted to a storage stable salt. This provides added flexibility to the overall process as the process steps leading up to the (S)-2-amino-6,6-dimethoxyhexanoic acid, methyl ester salt can be performed separately from the process steps for converting (S)-2-amino-6,6-dimethoxyhexanoic acid, methyl ester to the desired final product. The term storage stable salt refers to a salt of (S)-2-amino-6,6-dimethoxyhexanoic acid, methyl ester which can be maintained for a period of at least about 30 days under conditions of low temperature and the absence of moisture and then converted to (S)-2-amino-6,6-dimethoxy-hexanoic acid, methyl ester in high yields. Salts of (S)-2-amino-6,6-dimethoxyhexanoic acid, methyl ester of formula X suitable for this purpose include the oxalic acid salts (1:1) and (2:1), the diphenylacetic acid salt (1:1), and the phosphoric acid salt (1:1).

The salt is treated with a base such as potassium bicarbonate to give the (S)-2-amino-6,6-dimethoxyhexanoic acid, methyl ester of formula X.

As described by Robl in U.S. Pat. No. 5,508,272, (S)-2-amino-6,6-dimethoxyhexanoic acid, methyl ester of formula X can be coupled with the N-protected amino acid of the formula (V)

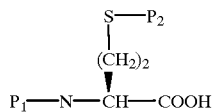

to give the dipeptide of the formula (VI)

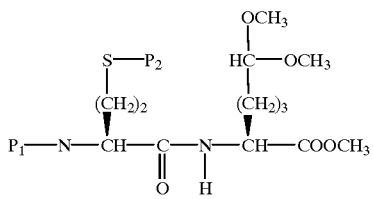

wherein $P_1$ is an amino protecting group such as benzyloxycarbonyl or t-butoxycarbonyl or a group which together with the N-atom forms a protecting group such as phthalimido and $P_2$ is a mercapto protecting group such as acetyl or benzoyl. This coupling reaction is preferably performed in the presence of a coupling reagent such as benzotriazol-1-yloxytris(dimethylamino)phosphonium hexafluorophosphate, ethyl-3-(3-dimethylamino)propyl carbodiimide, methanesulfonyloxybenzotriazole, or dicyclohexylcarbodiimide.

The $P_2$ protecting group is selectively removed from the dipeptide of formula VI such as by treatment with sodium methoxide in methanol or by treatment with p-toluenesulfonic acid in methanol. The resulting mercaptan compound is then subjected to an acid catalyzed cyclization reaction preferably by treating with a strong acid such as trifluoroacetic acid, p-toluenesulfonic acid, methanesulfonic acid, or a commercially available polystyrene sulfonate polymer type ion exchange resin such as Amberlyst15®. This cyclization reaction can be performed in a non-protic solvent such as methylene chloride or chloroform to give the lactam of the formula (VII)

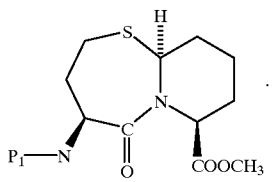

The lactam of formula VII is then treated to remove the $P_1$ N-protecting group and then reacted with the acylmercaptoalkanoyl sidechain of the formula (VIII)

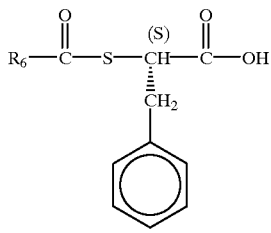

wherein $R_6$ is methyl or phenyl giving the compound of the formula (IX)

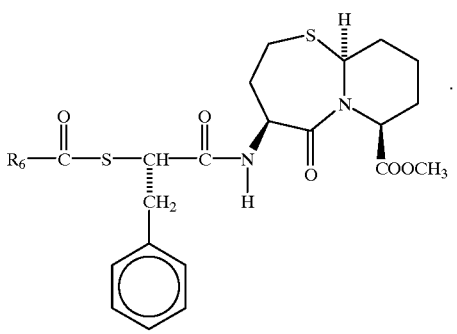

This coupling reaction can be performed in an organic solvent such as methylene chloride and in the presence of a coupling reagent such as 1-ethyl-3-(3-dimethylaminopropyl)carbodiimide, dicyclohexylcarbodiimide, benzotriazol-1-yloxytris-(dimethylamino)phosphonium hexafluorophosphate, carbonyldiimidazole, or 1-propanephosphoric acid, cyclic anhydride. Alternatively, the acylmercaptoalkanoic acid of formula VIII can be converted to an activated form prior to coupling such as an acid chloride, mixed anhydride, symmetrical anhydride, activated ester, etc.

The $P_1$ N-protecting group can be removed from the lactam of formula VII, for example, by treatment with hydrazine monohydrate when $P_1$ together with the N-atom forms a phthalimido group or by treatment with iodotrimethylsilane or palladium on carbon and hydrogen when $P_1$ is benzyloxycarbonyl or by treatment with hydrochloric acid in dioxane or other strong acid when $P_1$ is t-butoxycarbonyl.

The compound of formula IX is treated to remove the acyl group $R_6$-C(O)— and to convert the methyl ester to the carboxylic acid as shown in the desired final product of formula XI. For example, when $R_6$ is methyl, treatment with methanolic sodium hydroxide followed by aqueous acid yields the desired compound of formula XI.

4S-[4α(R*),7α,10aβ]]-Octahydro-4-[(2-mercapto-1-oxo-3-phenylpropyl)amino]-5-oxo-7H-pyrido[2,1-b][1,3]thiazepine-7-carboxylic acid possesses angiotensin converting enzyme and neutral endopeptidase inhibitory activity. This compound as well as its pharmaceutically acceptable salts are useful in treating cardiovascular diseases such as hypertension and congestive heart failure as note Robl U.S. Pat. No. 5,508,272. This compound can be administered to a mammalian host such as man at from about 0.1 mg to about 100 mg per kg of body weight per day, preferably from about 0.5 mg to about 25 mg per kg of body weight per day. The compound is preferably administered orally but parenteral routes and topical routes can also be employed. The daily dose can be administered singly or can be divided into two to four doses administered throughout the day.

The following examples are illustrative of the invention.

EXAMPLE 1

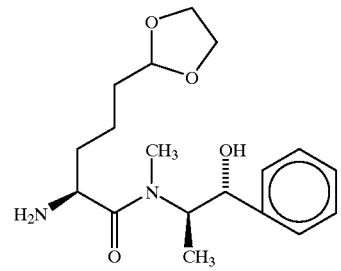

[αS-[αR*(1S*,2S*)]]-α-Amino-N-(2-hydroxy-1-methyl-2-phenylethyl)-N-methyl-1,3-dioxolane-2-pentanamide a) 2-(3-Iodopropyl)-1,3-dioxolane Sodium bicarbonate (4.0 g, 47.6 mmol) and sodium iodide (30.0 g, 0.20 mole, 2.4 eq.) were added to a solution of 2-(3-chloropropyl)-1,3-dioxolane (12.6 g, 83.66 mmol) in acetone (90 ml). The reaction vessel was fitted with a reflux condenser/argon inlet and briefly flushed with argon. The mixture was heated under argon in a 59° C. oil bath. After heating for 24 hours, the resulting mixture (golden yellow solution containing a white solid) was allowed to cool to room temperature. The mixture was then concentrated at reduced pressure to remove the bulk of the acetone. The residue was partitioned between heptane (about 400 ml) and water (about 100 ml). The organic fraction was washed with water (1×50 ml), 5% sodium bisulfite (3×50 ml, shaken vigorously), 1 N sodium bicarbonate (1×50 ml), and brine. After drying over magnesium sulfate, the solvent was removed at reduced pressure to give a colorless liquid (16.76 g) which was distilled to give 16.24 g of 2-(3-iodopropyl)-1,3-dioxolane as a colorless liquid; b.p. 75° C. (0.3 mm of Hg). TLC:Rf=0.25 (silica gel, hexane:ether, 4:1).

Anal. calc'd $C_6H_{11}IO_2$: C, 29.77; H, 4.58; I, 52.43

Found: C, 30.00; H, 4.61; I, 52.15.

b) [αS-[αR*(1S*, 2S*)]]-α-Amino-N-(2-hydroxy-1-methyl-2-phenylethyl)-N-methyl-1,3-dioxo-1ane-2-pentanamide A 0.5 liter, 4-necked, round-bottom flask, equipped with an overhead stirrer, thermocouple, addition funnel and a nitrogen inlet/outlet was charged with 11.4 g of lithium chloride (dried in vacuo at 130° C. for 6 hours and then at 100° C. for 18 hours prior to use), 9.1 g of diisoproylamine and 80 ml of tetrahydrofuran. After cooling to −78° C., a 2.5 M solution of n-butyllithium in hexanes (35 ml) was added over about 20 minutes while maintaining the temperature at less than or equal to −60° C. This mixture was allowed to stir at −78° C. for 45 minutes. A tetrahydrofuran solution of [R-(R*,R*)]-N-(2-hydroxy-1-methyl-2-phenylethyl)-N-methyl-α-aminoacetamide monohydrate [10 g., 0.04 mol, prepared as described by Myers et al., *Tetrahedron Letters*, Vol. 36, p. 4555–4558 (1995)] was added over 50 minutes while maintaining the temperature at less than or equal to −68° C. After the addition was complete, the mixture was stirred for an additional 45 minutes. The solution was allowed to warm to about 0° C. and held at that temperature for 45 minutes. The 2-(3-iodopropyl)-1,3-dioxolane (12 g) from part (a) was added as a tetrahydrofuran (10 ml) solution in one portion. After 3 hours reaction time at 0° C., TLC analysis indicated no observable starting material present and water (100 ml) was added as a quench. The tetrahydrofuran/hexane phase was separated from the lower aqueous phase. The aqueous phase was extracted with methylene chloride (4×100 ml). The methylene chloride phases were combined with the tetrahydrofuran/hexane phase and washed with 100 ml of brine. After drying over sodium sulfate and filtration, concentration in vacuo (bath temperature less than or equal to 40° C.) afforded an oil 9.57 g. The oil was chromatographed over silica gel 60 (column size: 3.5 cm×21 cm) eluting with 5% triethylamine in methylene chloride, collecting 100 ml fractions. Fractions number 6 through 12 were combined and concentrated in vacuo (bath temperature less than or equal to 45° C.) to afford an oil. This oil was dissolved in toluene (100 ml) and concentrated to remove residual triethylamine and give 4.54 g of the desired product as an oil.

Anal. calc'd for $C_{18}H_{28}N_2O_4$: C, 24.92; H, 8.35; N, 7.84 Found C, 25.12; H, 8.41; N, 7.49.

EXAMPLE 2

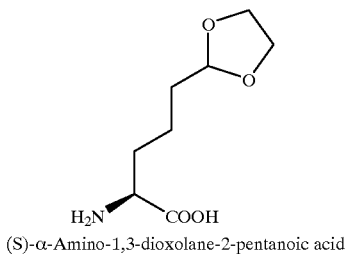

(S)-α-Amino-1,3-dioxolane-2-pentanoic acid

A 250 ml flask equipped with an argon inlet, magnetic stir bar and reflux condenser was charged with 5.9 g of the product from Example 1 and water (80 ml). The reaction was refluxed for seven hours and then allowed to stir overnight at room temperature. The reaction mixture was diluted with water (120 ml) and washed with methylene chloride (2×50 ml). The combined methylene chloride layers were extracted once with water (50 ml), and the combined aqueous layers were concentrated in vacuo. The residue was concentrated in vacuo from 100% ethanol (2×100 ml) to a solid. The solid was dissolved in water (15 ml) and the solution was stirred with a magnetic stir bar as 100% ethanol (150 ml) was added in a slow stream. Stirring was stopped, and the mixture was allowed to stand for one hour and then filtered. The solids were washed with 100% ethanol (2×25 ml), air-dried for 15 minutes, and then volatiles were removed under high vacuum overnight to give 2.0 g of the desired product as a white powder;

m.p. 224–226° (decomp.).

Anal. calcld for $C_8H_{15}NO_4$: C, 50.78; H. 7.99; N, 7.40 Found: C, 50.84; H, 8.18; N, 7.46.

EXAMPLE 3

The product of Example 2 was also prepared according to the following procedure.

A 0.5–1, 5-necked, round-bottom flask, equipped with an overhead stirrer, thermocouple, addition funnel and a nitrogen inlet/outlet was charged with diisopropylamine (45.52 g) and tetrahydrofuran (175 ml). After cooling to −5° C., a 2.49 m solution of freshly titrated n-butyllithium in hexanes (176.7 ml) was added while maintaining the temperature at −5° C. to 21° C. This mixture was allowed to stir at 21° C. for 45 minutes and was then cooled to −5° C. This cooled solution was added to a tetrahydrofuran (700 ml, −5° C.) slurry of [R-(R*,R*)]-N-(2-hydroxy-1-methyl-2-phenylethyl)-N-methyl-α-aminoacetamide monohydrate (50 g) and lithium chloride (57.21 g, was dried in vacuo at 130° C. for 6 hours and then at 100° C. for 18 hours prior to use) maintaining the temperature in the range −7° to 7° C. After the addition was complete, the mixture was stirred for an additional hour at 0° to 3° C. 2-(3-Iodopropyl)-1,3-dioxolane (51.72 g) was added to the reaction mixture as a tetrahydrofuran (50 ml) solution over 15 minutes with agitation. The reaction was stirred for 3 hours at 0° C. until it was determined to be complete (HPLC analysis). The reaction was quenched by the addition of water (450 ml) and the tetrahydrofuran/hexane phase was separated from the lower aqueous phase and set aside. The pH of the aqueous phase was adjusted from about 11 to about 8 by the addition of concentrated hydrochloric acid (10 ml) and then extracted with methylene chloride (2×250 ml). The methylene chloride phases were combined and concentrated in vacuo (bath temperature less than or equal to 40° C.) to afford [αS-[R*(1S*,2S*)]]-α-amino-N-(2-hydroxy-1-methyl-2-phenylethyl)-N-methyl-1,3-dioxolane-2-pentanamide as an oil (60 g). The oil was dissolved in water (300 ml) with heating and was refluxed for 12 hours until it was judged to be complete (HPLC analysis). After cooling, the reaction mixture was extracted with methylene chloride (2×250 ml) and the rich aqueous phase was concentrated in vacuo to afford the crude product as a yellow solid. The yellow solid was recrystallized from aqueous ethanol (water 75 ml, absolute ethanol 500 ml) and dried in vacuo to give 18.8 g of desired product as a white crystalline solid.

EXAMPLE 4

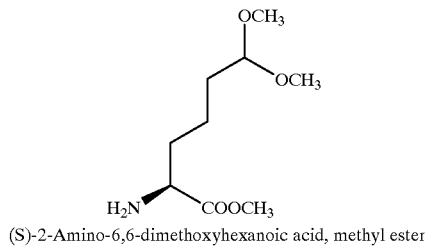

(S)-2-Amino-6,6-dimethoxyhexanoic acid, methyl ester

A 50-ml flask equipped with a magnetic stir bar was charged with anhydrous methanol (19 ml) and cooled to 0°

C. With rapid stirring thionyl chloride (0.63 ml) was slowly added to the methanol. The resulting solution was allowed to stir for 10 minutes, (S)-α-amino-1,3-dioxolane-2-pentanoic acid (1.25 g) was added, and the reaction was stirred to homogeneity. A reflux condenser was attached to the reaction flask. The cold bath was removed, and the reaction was heated at 40–45° C. for 8 hours and then allowed to stir for an additional 12 hours at room temperature. Triethylamine (4 ml) was added. The reaction was concentrated on a rotary evaporator in a 20° C. water bath to a solid. The solid was dissolved in half-saturated sodium bicarbonate (25 ml), and the solution was extracted with methylene chloride (6×8 ml). The combined methylene chloride layers were dried with a mixture of potassium carbonate and magnesium sulfate for 15 minutes, filtered, and concentrated on the rotary evaporator in a 20° C. water bath (after the bulk of the solvent had been removed, the residue was agitated on a rotary evaporator for an additional 20 minutes). The crude product (1.25 g) was isolated as a cloudy, yellow oil. TLC: $R_f$=0.55 (silica gel, 90% methylene chloride, 5% triethylamine, 5% methanol).

Anal. calcld for $C_9H_{19}NO_4$. 0.06 $C_2H_6O_3S$.0.02$CH_2Cl_2$ C, 51.39; H, 9.15; N, 6.56

Found: C, 51.19; H, 9.20; N, 6.52.

EXAMPLE 5

(S)-2-Amino-6,6-dimethoxyhexanoic acid, methyl ester

The product of Example 4 was also prepared according to the following procedure.

Under nitrogen, chlorotrimethylsilane (28.0 g) was added to a slurry of (S)-α-amino-1,3-dioxolane-2-pentanoic acid (20.9 g) and dimethyl sulfite (12.0 g) in methanol (240 ml) to afford a homogeneous solution. Following the observation of an exotherm to 29° C., the solution was heated to 40–45° C., stirred at that temperature for 8 hours and at about 22° C. for up to 72 hours. In-process HPLC analysis showed that the reaction was complete (about 93 M% conversion to product) and the resulting solution was cooled to –5 to –10° C. With stirring, the apparent pH of the mixture was adjusted to 11.7 to 11.9 by the slow careful addition of 32 wt. % (or 4.45 M) methanolic potassium methoxide solution (70 ml) maintaining the temperature in the range of –5 to 0° C. Analysis of the product slurry ($^1$H-NMR) indicated that the neutralizaiton was complete. The solvent of the product slurry was exchanged with ethyl acetate by first concentrating the thin slurry under vacuum at less than 30° C. to 300 ml volume followed by the addition of ethyl acetate until the removal of methanol was completed as judged by in-process GC analysis (less than 1 AP). Upon completion of the solvent exchange, the batch volume was adjusted to about 400 ml with ethyl acetate and the resulting slurry was filtered. Poly(acrylic acid co-acrylamide), potassium salt (3.0 to 3.2 g) and water (30–32 ml) were added to the filtrate. The mixture was stirred for about 35 minutes and filtered. Optionally, wet the poly (acrylic acid co-acrylamide), potassium salt treatment can be repeated on the filtrate if the quantity of ethylene glycol exceeds 0.15 equivalents, as judged by in-process GC analysis. Following in-process HPLC analysis, 17.4 g of the title product was obtained as an ethyl acetate solution in 80.8 M % yield.

EXAMPLE 6

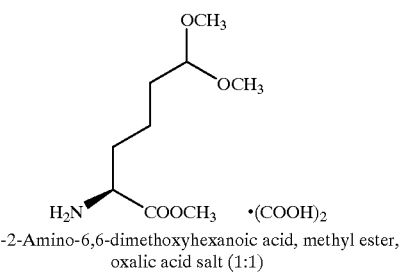

(S)-2-Amino-6,6-dimethoxyhexanoic acid, methyl ester, oxalic acid salt (1:1)

(S)-α-Amino-1,3-dioxolane-2-pentanoic acid (50 g, methanol (300 ml) and dimethyl sulfite (11.2 ml) were charged to a 250 ml, three neck flask equipped with a mechanical agitator, thermocouple, heating mantle, condenser, nitrogen inlet and vent. Chlorotrimethylsilane (83.9 ml) was added to the resulting slurry and the reaction mixture was heated at 40 to 42° C. for about 8 hours, followed by stirring at ambient temperature for 8 hours. Potassium bicarbonate (104.3 g) was slurried in methanol (200 ml) contained in a 2-liter three neck flask and the reaction mixture containing the hydrochloride salt of (S)-2-amino-6,6-dimethoxyhexanoic acid, methyl ester was neutralized by adding it to the potassium bicarbonate slurry while maintaining the pH of the mixture above 7. HyFlo® (12.5 g) and n-butyl acetate (400 ml) were added and the mixture was concentrated under vacuum (76 to 180 mm of Hg) to remove methanol while maintaining the temperature of the mixture below 30° C. tert-Butyl methyl ether (300 ml) was added to the slurry and after cooling to –5° C., the salts of neutralization were removed by filtration and the filter cake was washed with tert-butyl methyl ether (50 ml). The combined filtrates were warmed to 20 to 25° C. and a warm (approximately 27° C.) methanolic (73 ml) solution of oxalic acid dihydrate (36.7 g) was added portionwise over about 1 hour. The resulting slurry of (S)-2-amino-6,6-dimethoxyhexanoic acid, methyl ester, oxalic acid salt (1:1) was agitated for 30 minutes and additional product was crystallized by the slow addition of tert-butyl methyl ether (800 ml). After stirring the product slurry for 30 minutes, it was cooled to 0 to 5° C., held for at least 1 hour and filtered. The wet-cake was washed with tert-butyl methyl ether (2×300 ml) and dried under vacuum (about 200 mm Hg) at no more than 40° C. The desired product (62.5 g) was isolated as a white, free-flowing powder. Analytical data: HPLC: Tr=13.5 min (UV 205 nm): Rockland Technologies Inc., Zorbax CN 5 micron, 4.6×250 mm (product # 880952.705), 85 v/v% (0.01 M potassium phosphate solution):15 v/v% acetonitrile, 10 microliter injection volume eluted at 1.0 ml/min. The HPLC response was found to be linear in the range of 0.16 to 1.5 mg/ml. Samples were diluted with methanol or mobile phase.

Analytical data: $^1$H-NMR: 300 MHz; $CD_3OD$: δ1.3–1.6 (m, 4H), 1.8–2.0 (m, 2H), 3.3 (s, 6H), 3.8 (s, 3H), 4.1 (tr, 1H), 4.4 (tr, 1H) and 5.1 (br s, 3H). $^{13}$C-NMR: 75 MHz; δ21.03, 31.29, 33.06, 53.56, 53.65, 53.89, 105.74, 166.49 and 171.14.

EXAMPLE 7

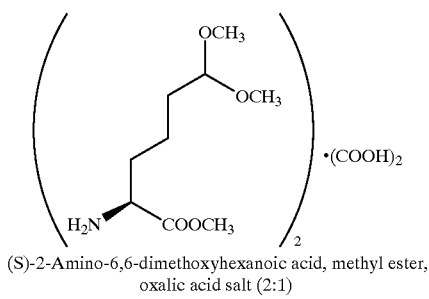

(S)-2-Amino-6,6-dimethoxyhexanoic acid, methyl ester, oxalic acid salt (2:1)

(S)-α-Amino-1,3-dioxolane-2-pentanoic acid (100 g), methanol (1200 ml) and dimethyl sulfite (44.8 ml) were charged to a 250 ml, three neck flask equipped with a mechanical agitator, thermocouple, heating mantle, condenser, nitrogen inlet, and vent. Chlorotrimethylsilane (168 ml) was added to the resulting slurry and the reaction mixture was heated at 40 to 42° C. for about 8 hours, followed by stirring at ambient temperature for 8 hours to afford a solution of (S)-2-amino-6,6-dimethoxyhexanoic acid, methyl ester, hydrochloride salt. Potassium bicarbonate (208.6 g) was slurried in methanol (400 ml) contained in a 5 liter three neck flask and the reaction containing the hydrochloride salt of (S)-2-amino-6,6-dimethoxyhexanoic acid, methyl ester was neutralized by adding it to the potassium bicarbonate slurry slowly over 1.5 hours while maintaining the pH of the mixture above 6.9. The solvent of the resulting slurry was replaced with n-butyl acetate by vacuum distillation (50 to 60 mm Hg and 30 to 40° C.) maintaining a pot volume of about 2 liters. After 2.25 liters of n-butyl acetate were distilled, methanol (1.25 l) was added to the distillation vessel and the distillation was continued, maintaining a pot volume of not less than 2 liters, until the water content of the slurry supernatant was less than 0.05 weight percent and the methanol level was less than 5 relative area percent by gas chromatography. Hexane (1.5 l) was charged to the resulting slurry and it was then cooled to −5° C. After stirring the mixture for 1 hours it was filtered and the filter-cake was washed with hexane (2×100 ml). The resulting hazy filtrate was polish filtered to afford a clear filtrate. The clear filtrate was warmed to 20 to 25° and a methanolic (1333 ml) solution of oxalic acid dihydrate (33.3 g) was added slowly over about 2 hours. The resulting slurry of (S)-2-amino-6,6-dimethoxy-hexanoic acid, methyl ester, oxalic acid salt (2:1) was agitated for 18 hours at ambient temperature and the product was collected on a filter. The product wet-cake was washed with acetonitrile (4×100 ml) and dried under vacuum at 45° C. to afford 103.2 g of the desired product.

Analytical data: HPLC: Tr=10.0 min (UV 205 nm): Rockland Technologies Inc., Zorbax stable bond CN, 5 micron, 4.6×250 mm, 85 v/v% (0.01 M potassium dihydrogen phosphate solution adjusted to pH 7.5 with KOH):15 v/v% acetronitrile 10 microliter injection volume eluted at 1.0 mL/min. Samples were diluted with methanol or mobile phase.

Analytical data: $^1$H-NMR: 300 MHz; $D_6$DMSO: δ1.2–1.4 (m, 2H), 1.4–1.6 (m, 2H) 1.6–1.8 (m, 2H), 3.2 (s, 6H), 3.55 (tr, lH), 3.7 (s, 3H), 4.3 (tr, 1 H) and 5.9 (br s, 4H). $^{13}$C-NMR: 75 MHz; δ21.00, 31.77, 32.08, 52.04, 52.39, 52.85, 103.75, 165.01 and 173.09.

EXAMPLE 8

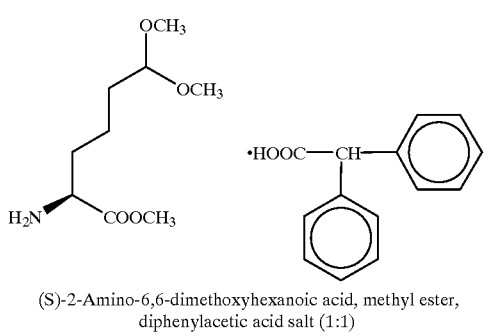

(S)-2-Amino-6,6-dimethoxyhexanoic acid, methyl ester, diphenylacetic acid salt (1:1)

Diphenylacetic acid (6.48 g) was dissolved, under nitrogen, in ethyl acetate (173 ml) at ambient temperature. An ethyl acetate/tert-butyl methyl ether (1:2) (185 ml) isolution of (S)-2-amino-6,6-dimethoxyhexanoic acid, methyl ester (6.27 g) was added to the diphenylacetic acid solution over 1 hour with stirring. Crystals of the salt precipitated immediately and the resulting thick slurry was diluted with tert-butyl methyl ether (100 ml) after about 65 ml of the aminoester solution had been added. The addition of tert-butyl methyl ether (100 ml) was repeated after about 140 ml of the aminoester solution was added. After addition of the aminoester solution was complete, the resulting slurry was stirred for 1.5 hours, the product was collected on a filter and air dried for 1 hour to afford 12.3 g of the title compound as a white crystalline solid.

Analytical data: $^1$H-NMR: 300 MHz; $CD_3OD$: δ1.4–1.6 (m, 2H), 1.7 (dd, 2H), 1.8–2.0 (m, 2H), 3.3 (s, 6H), 3.8 (s, 3H) , 4. 4 (tr, 1H) , 5.0 (s, 1H) and 7.1–7. 4 (m, 10H)

EXAMPLE 9

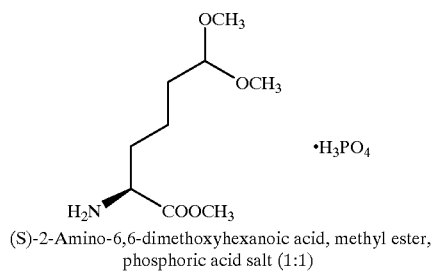

(S)-2-Amino-6,6-dimethoxyhexanoic acid, methyl ester, phosphoric acid salt (1:1)

A solution consisting of 85% phosphoric acid (5.2 ml) dissolved in methanol (35 ml) was added to a cooled (0 to 5° C.) ethyl acetate/tert-butyl methyl ether (3:2) (280 ml) solution of (S)-2-amino-6,6-dimethoxyhexanoic acid, methyl ester (9.33 g) over 15 minutes. Crystals of the salt precipitated immediately. The resulting slurry was stirred for 30 minutes at 0 to 5° C., the product was collected on a filter, washed with acetonitrile (50 ml) and dried under vacuum for 16 hours to afford 13.6 g of the title compound as a white crystalline solid.

What is claimed:

1. The compound of the formula (III)

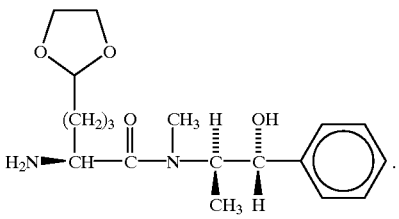

2. The compound of the formula (IV)

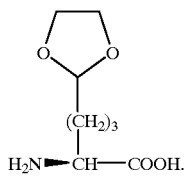

3. A process for preparing the compound of the formula (III)

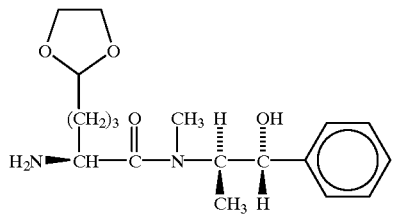

which comprises reacting the compound of the formula (I)

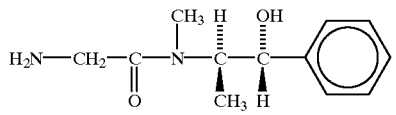

with the dioxolane of the formula (II)

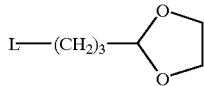

wherein L is a leaving group.

4. The process of claim 3 wherein:

L is selected from the group consisting of iodo, bromo, alkylsulfonyloxy, and arylsulfonyloxy.

5. The process of claim 4 wherein:

L is iodo; and the reaction between the glycinamide of forumula I and the dioxolane of formula II is performed in the presence of the lithium diisopropylamide.

6. A process for preparing the compound of the formula (IV)

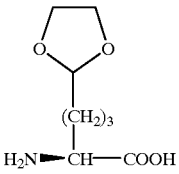

which comprises:

a) reacting the compound of the formula (I)

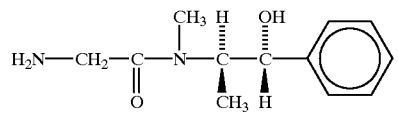

with the dioxolane of the formula (II)

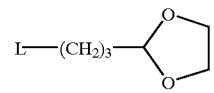

wherein L is a leaving group to give the compound of the formula (III)

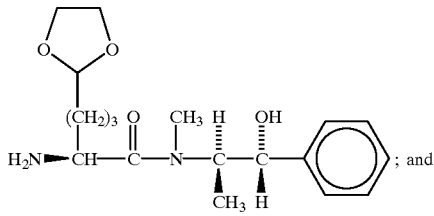; and b) treating the product of formula III with water under refluxing conditions to give the desired compound of formula IV.

7. The process of claim 6 wherein:

L is selected from the group consisting of iodo, bromo, alkylsulfonyloxy, and arylsulfonyloxy.

8. The process of claim 7 wherein:

L is iodo; and the reaction between the glycinamide of formula I and the dioxolane of formula II is performed in the presence of lithium diisopropylamide.

* * * * *